United States Patent [19]

Gumprecht et al.

[11] Patent Number: 4,843,181
[45] Date of Patent: Jun. 27, 1989

[54] PROCESS FOR THE MANUFACTURE OF 1,1,1-TRIFLUORODICHLOROETHANE AND 1,1,1,2-TETRAFLUOROCHLOROETHANE

[75] Inventors: William H. Gumprecht; Leo E. Manzer; V. N. Mallikarjuna Rao, all of Wilmington, Del.

[73] Assignee: E. I. Du Pont de Nemours and Company, Wilmington, Del.

[21] Appl. No.: 111,292

[22] Filed: Oct. 22, 1987

[51] Int. Cl.[4] .................. C07C 17/20; C07C 19/02
[52] U.S. Cl. ........................ 570/169; 423/595; 570/168
[58] Field of Search ............... 570/168, 169; 423/595

[56] References Cited

U.S. PATENT DOCUMENTS

| | | | |
|---|---|---|---|
| 2,458,551 | 1/1949 | Benning et al. | 570/168 |
| 2,576,823 | 11/1951 | Benning et al. | 570/168 |
| 3,183,276 | 5/1965 | Vecchio | 570/168 |
| 3,258,500 | 6/1966 | Swamer et al. | 260/653.7 |
| 3,755,477 | 8/1973 | Firth et al. | 260/653.4 |
| 3,803,241 | 4/1974 | Stolkin et al. | 570/168 |
| 4,748,285 | 5/1988 | Foulletier | 570/169 |

FOREIGN PATENT DOCUMENTS

| | | | |
|---|---|---|---|
| 72105 | 9/1973 | Japan | 570/168 |
| 1000485 | 8/1965 | United Kingdom . | |

*Primary Examiner*—J. E. Evans

[57] ABSTRACT

An improved gas-phase process for the manufacture of 1,1,1-trifluorodichloroethane and/or 1,1,1,2-tetrafluorochloroethane by contacting a suitable tetrahaloethylene and/or pentahaloethane with hydrogen fluoride in the presence of $Cr_2O_3$, prepared by pyrolysis of $(NH_4)_2Cr_2O_7$, the reaction being conducted under controlled conditions whereby the production of pentafluoroethane is minimized.

11 Claims, No Drawings

PROCESS FOR THE MANUFACTURE OF 1,1,1-TRIFLUORODICHLOROETHANE AND 1,1,1,2-TETRAFLUOROCHLOROETHANE

FIELD OF THE INVENTION

An improved process for the manufacture of 1,1,1-trifluorodichloroethane and/or 1,1,1,2-tetrafluorochloroethane, more particularly, a gas-phase reaction of a suitable tetrahaloethylene and/or pentahaloethane with hydrogen fluoride in the presence of a $Cr_2O_3$ catalyst prepared by pyrolysis of ammonium dichromate, the reaction being conducted under controlled conditions whereby the production of pentafluoroethane is minimized.

BACKGROUND OF THE INVENTION

Canadian Pat. No. 1,196,345 (1985) describes a process for the preparation of $CF_3CHXY$ (X=H, F; Y=H, F, Cl, Br, I) by addition of HF to the corresponding ethylene in the presence of chromium oxyfluoride at 20°–200° C., especially 60°–180° C.

U.S. Pat. No. 3,755,477 describes a process for producing fluorinated aliphatic hydrocarbons which comprises fluorinating a halogenated aliphatic hydrocarbon, including tetrachloroethylene and chlorotrifluoroethylene, by reaction in the gas phase with HF in the presence of a steam-treated and calcined chromium oxide catalyst prepared by a multi-step process. Example 23, column 5, shows tetrachloroethylene as a raw material with formation of $CF_3CHCl_2$ (20%), $CF_3CHClF$ (20%), $CF_3CHF_2$ (30%), and $CF_3CClF_2$ (20%) at 10/1 $HF/C_2Cl_4$ mol ratio, 5.4 seconds contact time and 360° C. reaction temperature. Example 24, column 5, shows chlorotrifluoroethylene as a raw material with formation of $CF_2=CF_2$ (20%) and $CF_3CHClF$ (13%) at 1.8/1 $HF/C_2ClF_3$ mol ratio, 4 seconds contact time and 320° C. reaction temperature. In these examples, less desirable pentafluorinated products are obtained in a greater amount than the desired tri- and tetrafluoro products.

U.S. Pat. No. 3,258,500 describes a process for the catalytic vapor phase reaction of HF with halohydrocarbons, including tetrachloroethylene and chlorotrifluoroethylene, employing a catalyst that consists essentially of a heat-activated anhydrous chromium (III) oxide which may be supported on alumina. This catalyst is highly active. Example 17, column 14 showing fluorination of tetrachloroethylene with this catalyst, like that of the above '477 patent, produces large quantities of the less desirable highly fluorinated pentafluoroethane. At 400° C. the product distribution is 35.0% pentafluoroethane, 9.2% 1-chloro-1,2,2,2-tetrafluoroethane, and 3.5% 1,1-dichloro-2,2,2-trifluoroethane. At 300° C. the product distribution is 38.3% 1-chloro-1,2,2,2-tetrafluoroethane, 25.4% pentafluoroethane, and 16.0% 1,1-dichloro-2,2,2-trifluoroethane. Example 20, column 15, shows that chlorotrifluoroethylene yields $CF_3CHF_2$ as the major product at 400° C.

GB No. 1,000,485 describes a process for the preparation of organic fluorinated compounds by fluorination of halo-olefins in the gaseous phase and at a temperature preferably withintthe range of 200° C. to 400° C. The catalyst consists essentially of partially fluorinated alumina impregnated with one or more polyvalent metal halides. The polyvalent metal may be chromium, cobalt, nickel or manganese. The total content of polyvalent metal halide, expressed as oxide, is not more than 15% by weight of the partially fluorinated (70-80%) alumina expressed as alumina. Example 4 (Table 4) shows that reaction of tetrachloroethylene with HF over such catalyst yields $CF_3CHCl_2$ as the major product at 220°–290° C. In addition, the patent states that, if fluorination of the catalyst is excessive, the activity of the catalyst is impaired (page 3, column 2, lines 85–87).

The references do not disclose how to favor the production of 1,1,1-trifluorodichloroethane over 1,1,1,2-tetrafluorochloroethane while maximizing the production of these two compounds taken together over the production of more highly fluorinated products.

The process of the instant invention achieves the desired high degree of selectivity by minimizing the formation of the pentafluoroethane through catalyst selection and control of the reaction variables, as discussed below and illustrated in the Examples.

SUMMARY OF THE INVENTION

What has been discovered is a process for the preparation of 1,1,1-trifluorodichloroethane and/or 1,1,1,2-tetrafluorochloroethane by fluorination of a tetrahaloethylene, $C_2Cl_{4-x}F_x$, wherein x=0 to 3, and/or a pentahaloethane, $C_2HCl_{5-x}F_x$, wherein x=0 to 2, comprising contacting in the gaseous phase at effective temperature, mol ratio, and contact time, said tetrahaloethylene and/or pentahaloethane with HF and $Cr_2O_3$, said $Cr_2O_3$ prepared by pyrolysis of $(NH_4)_2Cr_2O_7$, said contacting producing a product stream containing 1,1,1-trifluorodichloroethane and/or 1,1,1,2-tetrafluorochloroethane and pentafluoroethane, wherein the amount of said 1,1,1-trifluorodichloroethane and/or 1,1,1,2-tetrafluorochloroethane is greater than the amount of pentafluoroethane produced, and, thereafter, separating the 1,1,1-trifluorodichloroethane and/or 1,1,1,2-tetrafluorochloroethane from the product stream.

DETAILS OF THE INVENTION

The tetrahaloethylene of this invention is defined by the formula $C_2Cl_{4-x}F_x$, wherein x=0 to 3, and includes $CCl_2=CCl_2$, $CClF=CCl_2$, $CClF=CClF$, $CF_2=CCl_2$, and $CF_2=CClF$ and mixtures of these. The pentahaloethanes of this invention are defined by the formula $C_2HCl_{5-x}F_x$, wherein x=0 to 2, and includes $CCl_3CHCl_2$, $CCl_2FCHCl_2$, $CCl_3CHClF$, $CClF_2CHCl_2$, and $CCl_2FCHClF$ and mixtures of these. The tetrahaloethylenes and pentahaloethanes of this invention are known to the art.

The $Cr_2O_3$ catalyst of this invention is prepared by pyrolysis of ammonium dichromate. By pyrolysis is meant heating ammonium dichromate to a sufficient temperature and for a sufficient time to cause the following reaction to occur to substantial completion:

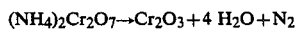

$$(NH_4)_2Cr_2O_7 \rightarrow Cr_2O_3 + 4 H_2O + N_2$$

For example, ammonium dichromate may be heated in a continuous kiln at 500°–700° C., preferably 540°–640° C., for 5–20 minutes so that it will undergo an internal oxidation-reduction reaction to produce mainly water, nitrogen and $Cr_2O_3$. After the water and nitrogen are driven off, the remaining fine powder of $Cr_2O_3$ may be cooled and compacted so as to increase its bulk density for ease of handling. For example, a bulk density of approximately 400–560 $kg/m^3$ may be desirable, preferably 448–512 $kg/m^3$.

The $Cr_2O_3$ obtained may contain low levels of contaminants which are present as a result of the manufacturing process for the original $(NH_4)_2Cr_2O_7$. Although not totally destructive of catalyst efficacy, potassium as a contaminant has an adverse effect on the activity and life of the catalyst of this invention. It is desirable for potassium levels to be 100 ppm by weight or less. The level may be reduced by a water washing step. While the conditions are not critical, the water washing step can include forming a slurry containing 5-15% $Cr_2O_3$, preferably 10%, and deionized water. Stirring of this water slurry can be carried out at 35°-65° C. for at least one hour, preferably two or more hours. The solids are then recovered by filtration, suitably on a plate and frame filter press. The filter cake can be analyzed for potassium. If its level is 100 ppm by weight or less (dry basis), the solids are, thereafter, dried. If not, the washing step can be repeated to obtain a desired level of potassium.

The form of the catalyst is not critical and may be used as pellets, powders or granules.

For example, if the catalyst is desired to be in the pellet form, 5-15%, preferably 10%, of chromium acetate and 1-5%, preferably 2%, of graphite can be added to the dried solids as pelletization aids. The chromium acetate can be added in aqueous solution of 30-70%, preferably 50% concentration. The resultant paste can be mulled to mix the ingredients and then pelletized to the desired size, preferably 0.32 cm × 0.32 cm cylinders. The pellets can be dried at 80°-120° C., preferably 105° C., for 8-48 hours, preferably 16-24 hours. The $Cr_2O_3$ pellets then have a bulk density of 1120-1440 kg/m$^3$ for the preferred pellet size and a surface area of 40-57 m$^2$/g, preferably 45-55 m$^2$/g. Pore volume is 0.15-0.3 cc/g, the potassium content is 100 ppm or less.

Generally, the resulting $Cr_2O_3$ will be pretreated with HF. It is thought that this converts some of the surface chrome oxide to chrome oxy-fluoride. This pretreatment can be accomplished by placing the $Cr_2O_3$ in a suitable container, which can be the reactor to be used to perform the reaction of the instant invention, and thereafter, passing HF over the pyrolyzed and dried $Cr_2O_3$ so as to partially saturate the $Cr_2O_3$ with HF. This is conveniently carried out by passing HF over the $Cr_2O_3$ for a period of time of, for example, about 15 to 300 minutes at a temperature of, for example, about 200° C. to about 450° C. The purpose of this pretreatment is to prevent damage to the catalyst due to possible high temperature excursions and resultant coking of the catalyst if the reactants, tetrahaloethylene and/or pentahaloethane, were contacted with the catalyst without first having conditioned some of the surface chrome oxide with HF. Nevertheless, this pretreatment is not essential; initial process conditions and equipment could be selected so as to avoid the problem of high temperature and coking of the catalyst.

The contacting of the reactants with HF in the presence of the catalyst, preferably pretreated, of the instant invention is performed at effective temperature, mol ratio and contact time. By effective temperature, mol ratio and contact time is meant the temperatures, mol ratios, and contact times which produce a product stream which contains an amount of 1,1,1-trifluorodichloroethane and/or 1,1,1,2-tetrafluorochloroethane which is greater than the amount of pentafluoroethane produced. The temperature can be, for example, about 225° C. to 400° C., preferably about 225° C. to 250° C., with a contact time, for example, of about 0.1 to 100 seconds, preferably about 10 to 90 seconds, and most preferably about 15 to 90 seconds.

The molar ratio of HF to the reactants can range, for example, from about 1/1 to 20/1, preferably about 3/1 to 10/1, and most preferably about 4/1 to 6/1.

In general, the higher the temperature, the greater the HF/reactant mol ratio, and the longer the contact time, the greater is the conversion of the reactants to fluorinated products and the greater is the degree of fluorination of the raw material. The above variables can be balanced, one against the other, so that formation of $CF_3CHCl_2$ is favored over $CF_3CHClF$, and the production of these two compounds taken together is maximized and that of more highly fluorinated products minimized.

A key feature of the invention is that through catalyst selection and process control, as described herein, the desired tri- and tetrafluoro products can be obtained as the major products at high reactant conversions, normally greater than 30%. Preferably, the reaction variables are controlled so as to keep the production of the pentafluoro product below about 10 area percent, as determined gas chromatographically, of the products produced. Thus, as illustrated in the Examples with tetrachloroethylene, the tri- and tetrafluoro products are obtained in very high yields while the production of higher fluorinated products is minimized, even at high conversions of tetrachloroethylene.

Intermediates formed during the course of the reaction, such as $CHClFCClF_2$, $CHCl_2CClF_2$, $CClF=CCl_2$ and $CHCl_2CCl_2F$ can be recycled to the reactor for the production of additional $CF_3CHCl_2$ and $CF_3CHClF$. In addition, $CF_3CHCl_2$ can be recycled to the reactor for the production of additional $CF_3CHClF$ when this is desired.

The reaction of the reactants with HF may be conducted in any suitable reactor, including fixed and fluidized bed reactors. The reaction vessel should be constructed from materials which are resistant to the corrosive effects of hydrogen fluoride such as "Hastelloy" and "Inconel".

The pentachloroethane may be fed directly to the reactor or may be prepared in-situ in the reactor by contemporaneously feeding trichloroethylene, chlorine and HF to the reactor containing the catalyst of this invention.

Pressure is not critical Atmospheric and superatmospheric pressures are the most convenient and are therefore preferred.

The fluorinated alkanes produced by the instant invention have utility as blowing agents, propellants and refrigerants. They can also be used as starting materials for the preparation of other useful compounds. For example, $CF_3CHClF$ can be used to prepare 1,1,1,2-tetrafluoroethane.

EXAMPLES

In the following illustrative Examples all parts and percentages are by weight and all temperatures are Centigrade unless otherwise stated. All reactions used commercial HF containing only trace amounts of water.

The pyrolyzed $Cr_2O_3$ catalyst used in the following Examples was prepared using ammonium dichromate having the following specifications:

| | |
|---|---|
| $(NH_4)_2Cr_2O_7$ | 99.5% |

| | | | | | |
|---|---|---|---|---|---|
| Insolubles | less than | 0.2% | | | |
| Iron | less than | 100 ppm | | | |
| Chloride | less than | 100 ppm | | | |
| Sulfate | less than | 500 ppm | | | |
| Alkali | less than | 2000 ppm | | | |
| pH (8 wt % aqueous sol). | | 3.2–4.0 | | | |

The preparation, drying and compacting of the $Cr_2O_3$ used in the following Examples were performed according to the following procedure:

A rotating continuous kiln, 18 inches in diameter and 17 feet long, was electrically heated to 570°–620° C. At this point the heater was turned off and ammonium dichromate was fed into the kiln at a feed rate of 280 lb/hr (residence time=8 minutes). The conversion of ammonium dichromate to $Cr_2O_3$ was essentially quantitative. The heat generated from the internal oxidation-reduction reaction to produce water, nitrogen and $Cr_2O_3$ was sufficient to maintain the desired reaction temperature. After the water and nitrogen were driven off, the remaining fine powder of $Cr_2O_3$ was cooled and compacted to a bulk density of approximately 448–512 kg/cubic meter.

PROCEDURE FOR PRETREATMENT

The reactor (0.5 inch ID, 12 inch long "Inconel" pipe) was charged with the amount of catalyst as described in the following Examples and placed in a sand bath. The bath was gradually heated to 400° while nitrogen gas at a flow rate of 50 ml/minute was passed through the reactor to remove traces of water. The temperature was lowered to 200°, and HF and nitrogen gas (1:4 molar ratio) were passed through the reactor. The nitrogen flow was decreased with time until neat HF was being passed through the reactor. At this point, the temperature was gradually raised to 450° and maintained there for 15 to 300 minutes.

PROCEDURE FOR FLUORINATION

The temperature was then decreased, while maintaining the HF flow, to the indicated values and, thereafter, $CCl_2=CCl_2$ flow was started. The flows of HF and $CCl_2=CCl_2$ were adjusted to give the indicated molar ratios and contact times.

The reactor effluent was scrubbed with aqueous potassium hydroxide to remove HCl and HF, and sampled on-line with a gas chromatograph using a 20 foot, long one-eighth inch diameter column containing "Krytox" perfluorinated polyether on an inert support and a helium carrier gas flow of 35 cc/minute.

EXAMPLES 1–7

The Procedures for Pretreatment and Fluorination were followed using 38.1 g (30 cc) of $Cr_2O_3$ with a potassium content of 60 ppm as the initial catalyst charge in the form of crushed pellets (40–80 mesh). The results are given in the Table.

TABLE

| | Example | | | | | | |
|---|---|---|---|---|---|---|---|
| | 1 | 2 | 3 | 4 | 5 | 6 | 7 |
| Temperature | 300° | 300° | 250° | 225° | 225° | 225° | 250° |
| HF/$C_2Cl_4$ mol ratio | 4/1 | 4/1 | 4/1 | 6/1 | 10/1 | 6/1 | 6/1 |
| Contact time (sec.) | 15 | 30 | 60 | 60 | 60 | 90 | 90 |
| Conversion (percent) | 79.8 | 89.4 | 97.8 | 94.9 | 90.4 | 98.3 | 99.5 |
| Area Percent | | | | | | | |
| $CF_3CHCl_2$ | 65.3 | 57.9 | 76.1 | 73.1 | 74.2 | 78.3 | 68.3 |
| $CF_3CHClF$ | 11.8 | 13.2 | 14.5 | 10.0 | 10.0 | 12.4 | 20.2 |
| $CF_3CHF_2$ | 10.7 | 15.1 | 5.4 | 0.1 | 0.1 | 0.1 | 8.0 |
| $CF_3CHCl_2+$ $CF_3CHClF$ | 77.1 | 71.1 | 90.6 | 83.1 | 84.2 | 90.7 | 88.5 |

We claim:

1. A process for the preparation of 1,1,1-trifluorodichloroethane and/or 1,1,1,2-tetrafluorochloroethane by fluorination of a tetrahaloethylene, $C_2Cl_{4-x}F_x$, wherein x=0 to 3, and/or pentahaloethane, $C_2HCl_{5-x}F_x$, wherein x=0 to 2, comprising
   contacting in the gaseous phase at effective temperature, mol ratio and contact time, said tetrahaloethylene and/or pentahaloethane with HF and $Cr_2O_3$, said $Cr_2O_3$ prepared by pyrolysis of $(NH_4)_2Cr_2O_7$, said contacting producing a product stream containing 1,1,1-trifluorodichloroethane and/or 1,1,1,2-tetrafluorochloroethane and pentafluoroethane, wherein the amount of said 1,1,1-trifluorodichloroethane and/or 1,1,1,2-tetrafluorochloroethane produced is greater than the amount of pentafluoroethane produced and, thereafter,
   separating the 1,1,1-trifluorodichloroethane and/or 1,1,1,2-tetrafluorochloroethane from the product stream.

2. The process of claim 1 wherein the tetrahaloethylene is tetrachloroethylene.

3. The process of claim 1 wherein the HF is contacted with the tetrahaloethylene and/or pentahaloethane at a mol ratio of about 1/1 to about 20/1, at a temperature of about 225° C. to about 400° C., and a contact time of about 0.1 seconds to about 100 seconds.

4. The process of claim 3 wherein the HF is contacted with the tetrahaloethylene and/or pentahaloethane at a mol ratio of about 3/1 to about 10/1, at a temperature of about 225° C. to about 250° C., and a contact time of about 10 seconds to about 90 seconds.

5. The process of claim 4 wherein the HF is contacted with the tetrahaloethylene and/or pentahaloethane at a mol ratio of about 4/1 to about 6/1, at a temperature of about 225° C. to about 250° C., and a contact time of about 15 seconds to about 90 seconds.

6. The process of claim 1 wherein conversion of the tetrahaloethylene and/or pentahaloethane to fluorinated products is between about 30% and 100%.

7. The process of claim 1 wherein the amount of pentafluoroethane in the product stream is less than 10 area percent by gas chromatography.

8. The process of claim 1 further comprising the step of recycling at least a portion of starting materials and underfluorinated products.

9. The process of claim 1 wherein the $Cr_2O_3$ contains 100 ppm potassium or less.

10. The process of claim 1 wherein before the contacting step, the $Cr_2O_3$ is given a pretreatment by passing hydrogen fluoride gas over it.

11. The process of claim 10 wherein the pretreatment is carried out for about 15 to about 300 minutes at about 200° C. to about 450° C.

* * * * *